United States Patent
Kita et al.

(10) Patent No.: US 8,748,189 B2
(45) Date of Patent: Jun. 10, 2014

(54) METHOD AND APPARATUS FOR MEASURING BROMATE IONS

(75) Inventors: Natsumi Kita, Tokyo (JP); Eri Hasegawa, Tokyo (JP)

(73) Assignee: Metawater Co., Ltd., Tokyo (JP)

( * ) Notice: Subject to any disclaimer, the term of this patent is extended or adjusted under 35 U.S.C. 154(b) by 0 days.

(21) Appl. No.: 13/597,664

(22) Filed: Aug. 29, 2012

(65) Prior Publication Data
US 2013/0337572 A1   Dec. 19, 2013

(51) Int. Cl.
*G01N 21/75* (2006.01)
*G01N 21/00* (2006.01)

(52) U.S. Cl.
USPC .......................................................... 436/124

(58) Field of Classification Search
USPC .......................................................... 436/124
See application file for complete search history.

(56) References Cited

U.S. PATENT DOCUMENTS

2010/0330694 A1*  12/2010  Igarashi et al. ............... 436/172

FOREIGN PATENT DOCUMENTS

JP    09-119925      5/1997
WO   2009/116554 A1  9/2009

OTHER PUBLICATIONS

Hatzistavros Vasilios S. et al, Bromate Determination in Water after Membrane Complexation and Total X-ray Fluorescence Analysis, Anal. Chem., 2007, 79, 2827-2832.*

* cited by examiner

*Primary Examiner* — Christine T Mui
(74) *Attorney, Agent, or Firm* — Burr & Brown, PLLC

(57) ABSTRACT

A method for measuring bromate ion includes: a first step of introducing a test water sample to an anion exchanger that selectively absorbs bromate ions; a second step of introducing, to the anion exchanger, a hydrochloric acid solution containing a fluorescent substance, a fluorescence intensity of which is changed by the coexistence of bromate ions; a third step of measuring the fluorescence intensity of the fluorescent substance contained in the hydrochloric acid solution discharged from the anion exchanger; and a fourth step of using a calibration curve, which shows a relationship between the fluorescence intensity of the fluorescent substance and the concentration of the bromate ions, to calculate the concentration of the bromate ions that corresponds to the measured fluorescence intensity.

5 Claims, 8 Drawing Sheets

METHOD AND APPARATUS FOR MEASURING BROMATE IONS

CROSS REFERENCE TO RELATED APPLICATION

The present application claims the benefit of priority from Japanese Patent Application No. 2012-136846 filed Jun. 18, 2012, the entire content of which is incorporated herein by reference.

BACKGROUND OF THE INVENTION

1. Field of the Invention

The present invention relates to a bromate ion measuring method and apparatus for measuring the concentration of bromate ions in a test water sample.

2. Description of the Related Art

Bromide ions ($Br^-$) are contained in raw waters, such as river water. When the water is treated by the ozonated process, bromide ions react with ozone to generate bromate ions ($BrO_3^-$). It is considered that bromate ions are a carcinogen. Thus, the WHO (World Health Organization) provides that the guideline value of the concentration of bromate ions in drinking water is 10 µg/L. In Japan, a revision was made about a ministerial ordinance concerning water quality standard that was issued on May 30, 2003, and the revised ordinance provides that the standard value of the concentration of bromate ions in drinking water is 10 µg/L.

As a method for measuring the bromate ion concentration in water, known is an ion chromatography with post-column reaction (IC-PC method). The IC-PC method is a method of using an anion exchange column to separate bromate ions in a test water sample, adding sulfuric acid, and a mixed liquid of sodium nitrite and sodium bromide to the eluate of the bromate ions, thereby converting the bromate ions to tribromide ions, and then measuring the ultraviolet absorbance of the tribromide ions to determine the bromate ions quantitatively. In this IC-PC method, two-stage reactions take place, and it is necessary to convert, in the first-stage reaction thereof, bromic acid into tribromide ions with a potassium-bromide/sulfuric-acid solution, and using, in the second-stage reaction, a sodium nitrite solution to ensure the linearity of a calibration curve in a low concentration range thereof. Thus, an operation for measuring the bromate ion concentration according to the IC-PC method is complicated, and it is difficult to apply this method to a process apparatus.

In light of such a background, in recent years, a suggestion has been made about a method of using fluorescence intensity to measure the concentration of bromate ions. In this method, to a test water sample, trifluoperazine (TFP), which is a fluorescent substance that is reactive by the co-existence thereof with bromate ions, and hydrochloric acid are added, the fluorescence intensity is measured at an excitation wavelength of 300 nm and an emission wavelength of 480 nm, and then a calculation is made about the difference in fluorescence intensity between the test water sample and a standard sample containing no bromate ion. From the use of a calibration curve of fluorescence intensity difference and the concentration of bromate ions, and the fluorescence intensity difference of the test water sample calculated above, the bromate ion concentration is measured. According to this method, bromate ions can be easily and rapidly measured with a high precision.

In the meantime, TFP shows a quenching reaction when the excitation wavelength, and the emission wavelength for measurement are 300 nm and 480 nm, respectively. However, when the excitation wavelength and the emission wavelength for measurement are 300 nm and 480 nm, respectively, the optimal concentration of hydrochloric acid that makes it possible to ensure the linearity of the calibration curve is a very high value of 6 N. Therefore, in the conventional method, wherein the hydrochloric acid concentration used for the measurement is high, the apparatus (concerned) is easily corroded, and running costs increase. Furthermore, under this measuring condition, the slope value of the calibration curve is changed by co-existing nitrate ions, so that the bromate ion concentration is not precisely measured in some cases. In light of such a background, it has been expected to provide a technique making it possible to measure the concentration of bromate ions precisely without being affected by coexisting substances while the concentration of hydrochloric acid necessary for the measurement is lowered.

SUMMARY OF THE INVENTION

A method for measuring bromate ion according to the present invention includes: a first step of introducing a test water sample to an anion exchanger that selectively absorbs bromate ions; a second step of introducing, to the anion exchanger, a hydrochloric acid solution containing a fluorescent substance, a fluorescence intensity of which is changed by the coexistence of bromate ions; a third step of measuring the fluorescence intensity of the fluorescent substance contained in the hydrochloric acid solution discharged from the anion exchanger; and a fourth step of using a calibration curve, which shows a relationship between the fluorescence intensity of the fluorescent substance and the concentration of the bromate ions, to calculate the concentration of the bromate ions that corresponds to the measured fluorescence intensity, wherein the third step comprises the step of measuring the fluorescence intensity at any one of a case where the excitation wavelength and the emission wavelength are 264 nm and 400 nm, respectively, a case where the excitation wavelength and the emission wavelength are 264 nm and 480 nm, respectively, and a case where the excitation wavelength and the emission wavelength are 300 nm and 400 nm, respectively.

An apparatus for measuring bromate ion according to the present invention includes: a unit that introduces a test water sample to an anion exchanger that selectively absorbs bromate ions; a unit that introduces, to the anion exchanger, a hydrochloric acid solution containing a fluorescent substance, a fluorescence intensity of which is changed by the coexistence of bromate ions; a unit that measures the fluorescence intensity of the fluorescent substance contained in the hydrochloric acid solution introduced to the anion exchanger; and a unit that uses a calibration curve, which shows a relationship between the fluorescence intensity of the fluorescent substance and the concentration of the bromate ions, to calculate the concentration of the bromate ions that corresponds to the measured fluorescence intensity, wherein the fluorescence intensity measuring unit makes a measurement of the fluorescence intensity at any one of a case where the excitation wavelength and the emission wavelength are 264 cm and 400 nm, respectively, a case where the excitation wavelength and the emission wavelength are 264 nm and 480 nm, respectively, and a case where the excitation wavelength and the emission wavelength are 300 nm and 400 nm, respectively.

DETAILED DESCRIPTION OF THE INVENTION

Figure 1A:
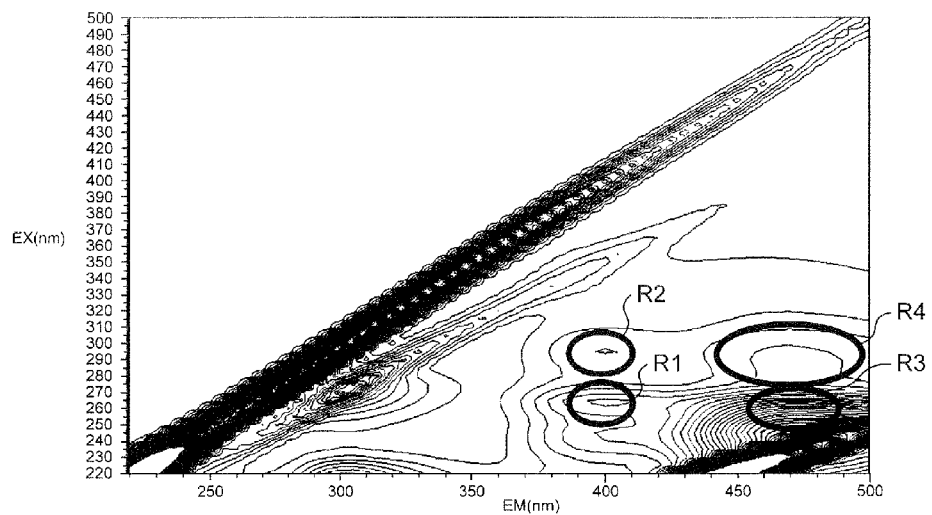
FIG. 1A is a chart showing an excitation emission matrix of TFP which has been obtained by adding a TFP solution to a test water sample having a bromate ion concentration of 0 μg/L, and then adding hydrochloric acid thereto, thereby making the water into an acidic condition.

Hereinafter, referring to the drawings, a description will be made about a method for measuring bromate ions that is an embodiment of the invention.

Figure 1B:
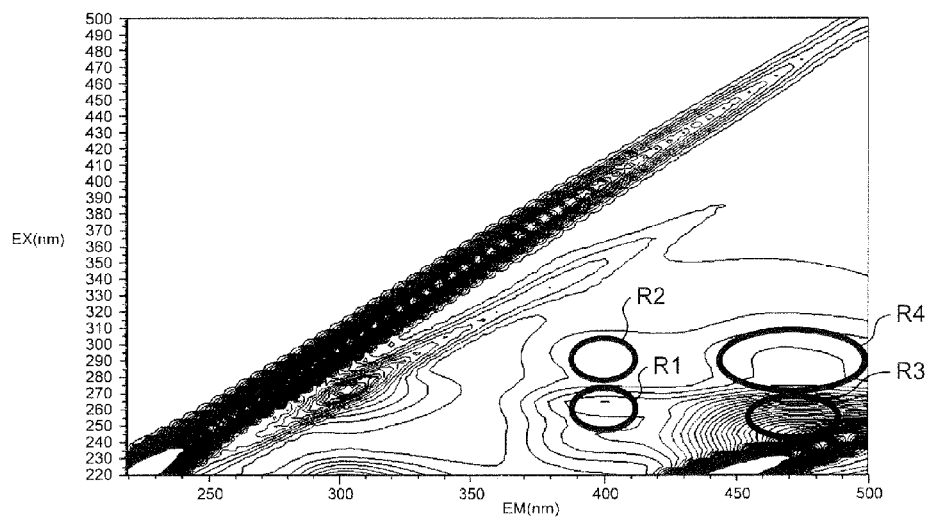
FIG. 1B is a chart showing an excitation emission matrix of TFP which has been obtained by adding a TFP solution to a test water sample having a bromate ion concentration of 20 μg/L, and then adding hydrochloric acid thereto, thereby making the water into an acidic condition.

The inventors of the present invention have repeated eager researches to find out that the fluorescence intensity of TFP is changed also in cases other than a case where the excitation wavelength and the emission wavelength are 300 nm and 480 nm, respectively. Specifically, FIGS. 1A and 1B are charts showing excitation emission matrixes of TFP which have been respectively obtained by adding a TFP solution (294 μM) to test water samples having a bromate ion concentration of 0 μg/L and 20 μg/L, respectively, and then adding hydrochloric acid thereto, thereby making the waters into an acidic condition. The excitation emission matrixes have been measured, using spectrophotofluorometer, RF-5300PC, manufactured by Shimadzu Corp., and a spectrophotofluorometer, F-2700, manufactured by Hitachi High-Technologies Corp.

As is evident from a comparison between FIGS. 1A and 1B, a peak of the excitation emission matrix in the case where bromate ions are present in a test water sample is measured when the excitation wavelength and the emission wavelength are 264 nm and 400 nm (region R1), respectively, as well as when the excitation wavelength and the emission wavelength are 300 nm and 400 nm (region R2), respectively, when the excitation wavelength and the emission wavelength are 264 nm and 480 nm (region R3), respectively, and the excitation wavelength and the emission wavelength are 300 nm and 480 nm (region R4), respectively.

Figure 2:
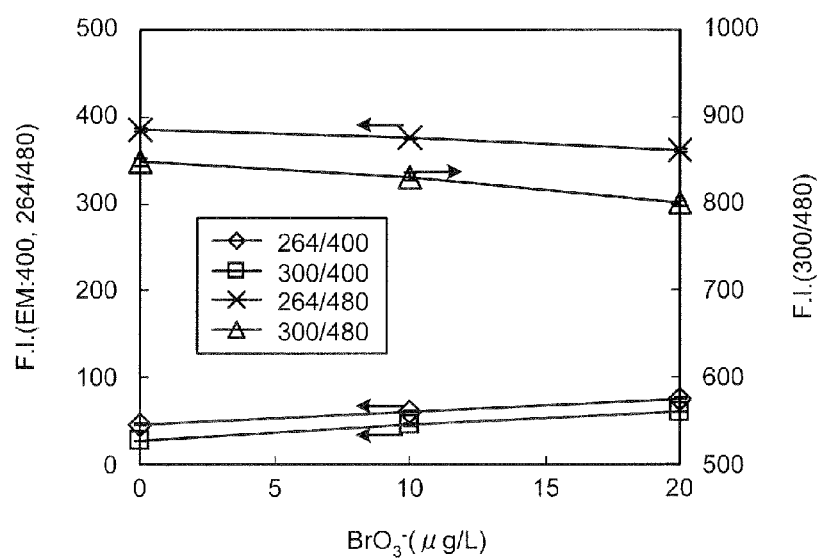
FIG. 2 is a graph showing a change in the fluorescence intensity (F. I.) relative to a change in the concentration of bromate ions for respective wavelengths when the concentration of hydrochloric acid is 6 mol/L.

Thus, the inventors have analyzed a change in the fluorescence intensity relative to a change in the bromate ion concentration at the excitation wavelength and the emission wavelength at which each of the peaks of the excitation emission matrix is measured (hereinafter, the respective excitation wavelengths and emission wavelengths at these peaks will be referred to as the peak wavelengths). FIG. 2 is a graph showing a change in the fluorescence intensity (F. I.) relative to a change in the bromate ion concentration for respective peak wavelengths. As shown in FIG. 2, it has been verified that when the emission wavelength is 480 nm (the peak wavelength in each of the regions R3 and R4), there is caused a quenching reaction giving a fluorescence intensity decreased as the bromate ion concentration is increased. On the other hand, it has been verified that when the emission wavelength is 400 nm (the peak wavelength in each of the regions R1 and R2), there is caused a fluorescence reaction giving a fluorescence intensity increased as the bromate ion concentration is increased.

Figure 3A:
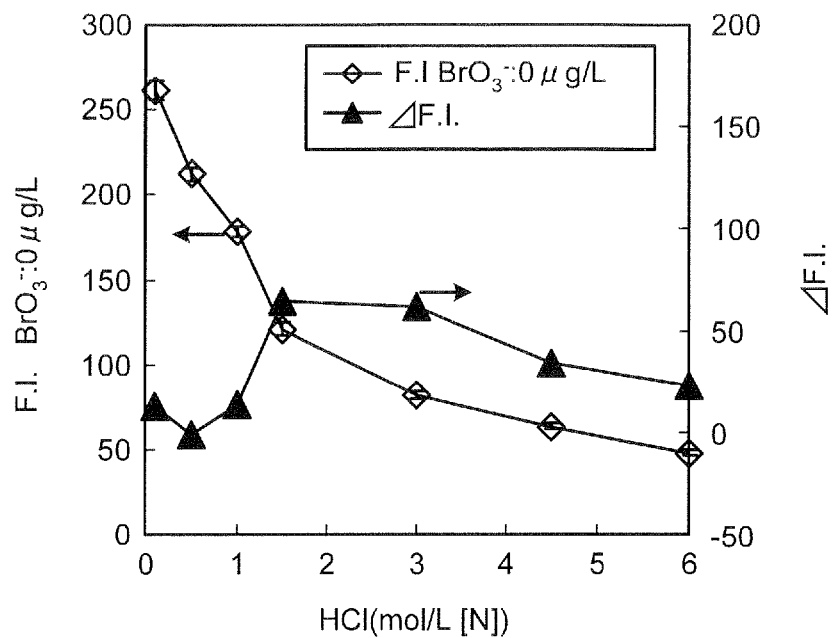
FIG. 3A is a graph showing the following in a case where the excitation wavelength and the emission wavelength are 264 nm and 400 nm: a change in the fluorescence intensity (F. I.) following a change in the concentration of hydrochloric acid when the concentration of bromate ion is 0 μg/L; and a change in the absolute value of the fluorescence intensity difference between the fluorescence intensity when the bromate ion concentration is 0 μg/L and that when the bromate ion concentration is 20 μg/L (ΔF. I.)
Figure 3B:
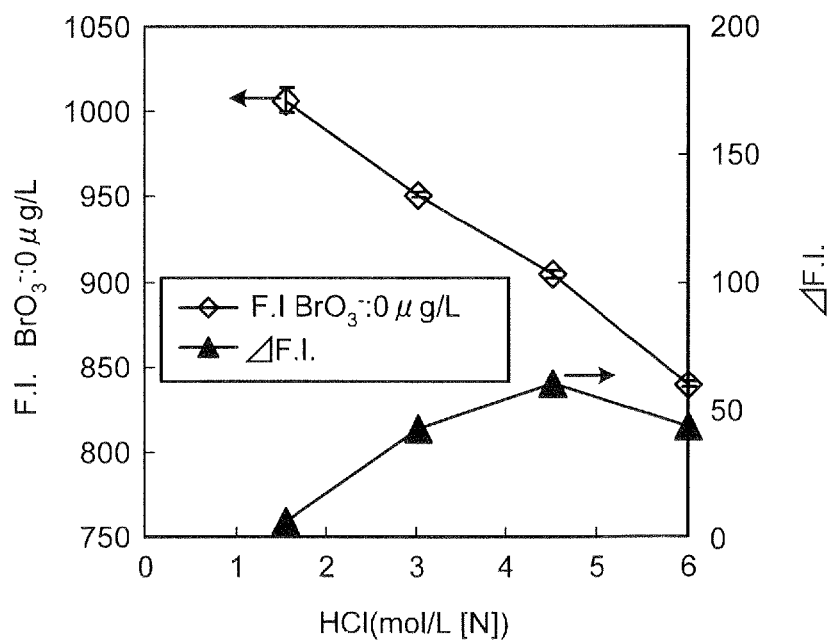
FIG. 3B is a graph showing the following in a case where the excitation wavelength and the emission wavelength are 300 nm and 480 nm: a change in the fluorescence intensity (F. I.) following a change in the concentration of hydrochloric acid when the concentration of bromate ion is 0 μg/L; and a change in the absolute value of the fluorescence intensity difference between the fluorescence intensity when the bromate ion concentration is 0 μg/L and that when the bromate ion concentration is 20 μg/L (ΔF. I.)

Next, the inventors have evaluated the optimal hydrochloric acid concentration when the excitation wavelength and the emission wavelength are 264 nm and 400 nm, respectively, as well as when the excitation wavelength and the emission wavelength are 300 nm and 480 nm, respectively. FIG. 3A is a graph showing the following in a case where the excitation wavelength and the emission wavelength are 264 nm and 400 nm: a change in the fluorescence intensity (F. I.) following a change in the concentration of hydrochloric acid when the concentration of bromate ions is 0 μg/L; and a change in the absolute value of the fluorescence intensity difference between the fluorescence intensity when the bromate ion concentration is 0 μg/L and that when the bromate ion concentration is 20 μg/L (ΔF. I.). FIG. 3B is a graph showing the same in a case where the excitation wavelength and the emission wavelength are 300 nm and 480 nm.

As shown in FIG. 3B, when the excitation wavelength and the emission wavelength are 300 nm and 480 nm, which are conventional measuring wavelengths, the fluorescence intensity difference relative to the change in the hydrochloric acid concentration is maximum in a range that the hydrochloric acid concentration is from 4.5 to 6 mol/L [N], and the linearity is also kept in this range. Although the optimal hydrochloric acid concentration ranges from 4.5 to 6 mol/L [N], a sufficient reproducibility is not obtained at the concentration of 4.5 mol/L [N]. Thus, the hydrochloric acid concentration optimal for the reproducibility is determined to be 6 mol/L [N]. In the meantime, as shown in FIG. 3A, when the excitation wavelength and the emission wavelength are 264 nm and 400 nm, which are one of the newly identified peak wavelengths, the fluorescence intensity difference relative to the change in the hydrochloric acid concentration is maximum in a range that the hydrochloric acid concentration is from 1.5 to 3 mol/L [N], and further the linearity is also kept in this range. Although the optimal hydrochloric acid concentration is in the range of 1.5 to 3 mol/L [N], the optimal hydrochloric acid concentration is determined to be 3 mol/L [N] from the viewpoint of the reproducibility.

From the above matter, it has been found out that when the excitation wavelength and the emission wavelength are set to 264 nm and 400 nm, respectively, the hydrochloric acid concentration can be lowered to about ½ of the conventional hydrochloric acid concentration. It has also been found out, though not shown in figures, that also when the excitation wavelength and the emission wavelength are 264 nm and 480 nm, respectively, as well as when the excitation wavelength and the emission wavelength are 300 nm and 400 nm, respectively, the hydrochloric acid concentration can be lowered in the same way. Accordingly, when the fluorescence intensity can be measured at any one of a case where the excitation wavelength and the emission wavelength are 264 nm and 400 nm, respectively, a case where the excitation wavelength and the emission wavelength are 300 nm and 400 nm, respectively, and a case where the excitation wavelength and the emission wavelength are 264 nm and 480 nm, respectively, the concentration of hydrochloric acid necessary for the measurement can be lowered.

Figure 4:
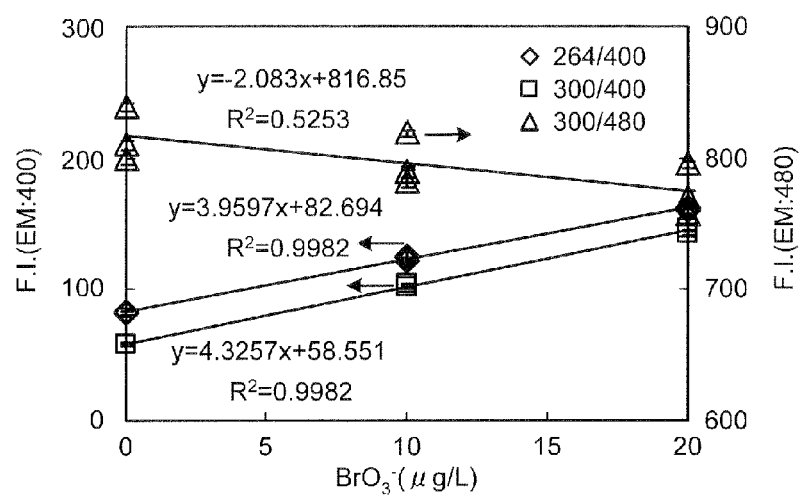
FIG. 4 is a graph demonstrating calibration curves for the fluorescence intensity (F. I.) and the bromate ion concentration obtained when the hydrochloric acid concentration is the optimal hydrochloric acid concentration for respective peak wavelengths.

FIG. 4 is a graph demonstrating results obtained by measuring, plural times, the fluorescence intensity (F. I.) relative to a change in the bromate ion concentration at the optimal hydrochloric acid concentration for the above-mentioned peak wavelengths. As shown in FIG. 4, when the emission wavelength is 480 nm, a variability in the fluorescence intensity is large and the slope value of the calibration curve also fluctuates. However, when the emission wavelength is 400 nm, a variability in the fluorescence intensity is small and the slope value does not fluctuate. For this reason, the fluorescence intensity is measured at a reaction temperature equivalent to that under the reaction condition in the prior art.

Figure 5A:
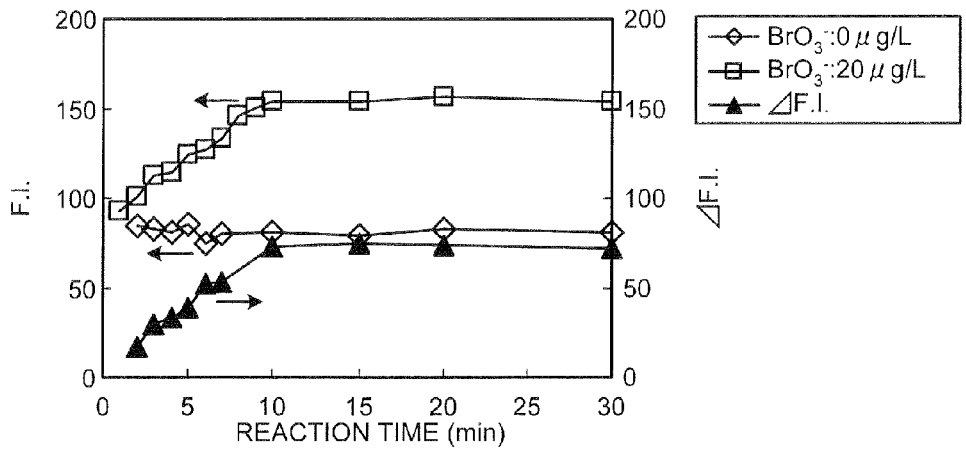
FIG. 5A is a graph showing the following about test water samples having bromate ion concentrations of 0 μg/L and 20 μg/L, respectively, in a case where the excitation wavelength and the emission wavelength are 264 nm and 400 nm: a change in the fluorescence intensity (F. I) with reaction time; and a change in the absolute value of the fluorescence intensity difference between the fluorescence intensity when the bromate ion concentration is 0 μg/L and that when the bromate ion concentration is 20 μg/L (ΔF. I.)
Figure 5B:
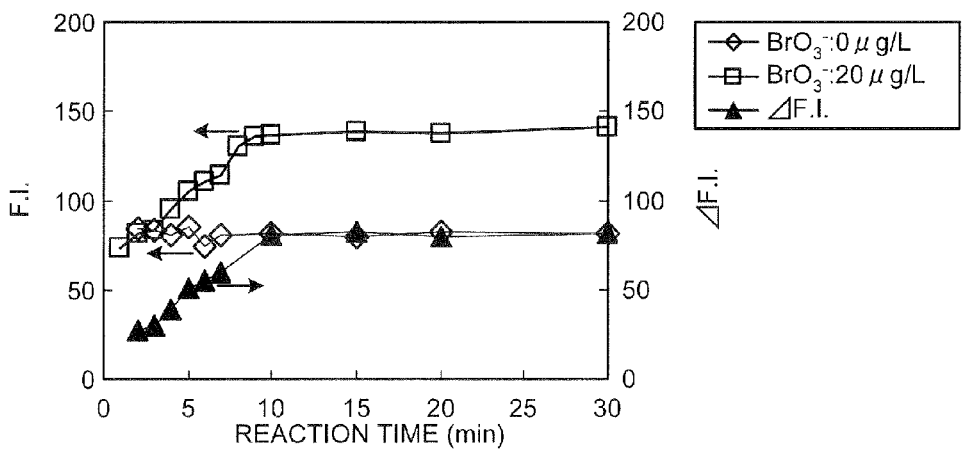
FIG. 5B is a graph showing the following about test water samples having bromate ion concentrations of 0 μg/L and 20 μg/L, respectively, in a case where the excitation wavelength and the emission wavelength are 300 nm and 400 nm: a change in the fluorescence intensity (F. I) with reaction time; and a change in the absolute value of the fluorescence intensity difference between the fluorescence intensity when the bromate ion concentration is 0 μg/L and that when the bromate ion concentration is 20 μg/L (ΔF. I.)
Figure 5C:
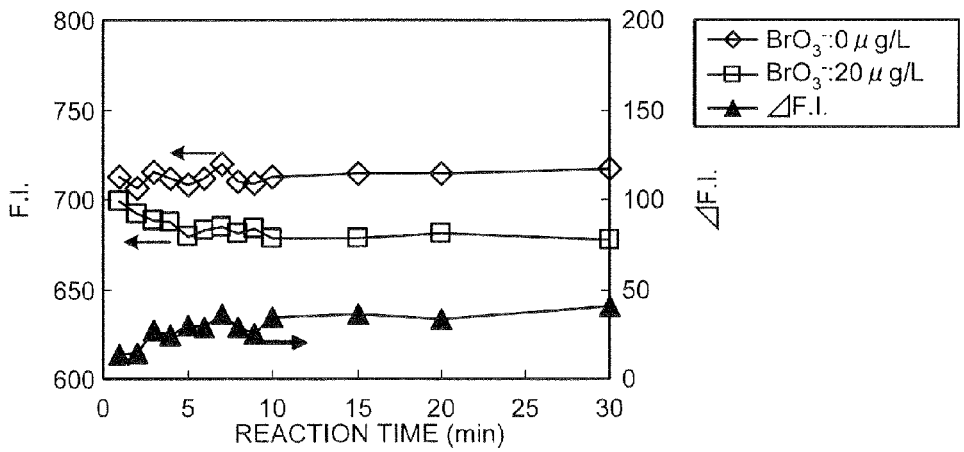
FIG. 5C is a graph showing the following about test water samples having bromate ion concentrations of 0 μg/L and 20 μg/L, respectively, in a case where the excitation wavelength and the emission wavelength are 300 nm and 480 nm: a change in the fluorescence intensity (F. I) with reaction time; and a change in the absolute value of the fluorescence intensity difference between the fluorescence intensity when the bromate ion concentration is 0 μg/L and that when the bromate ion concentration is 20 μg/L (ΔF. I.)

FIG. 5A is a graph showing the following about test water samples having bromate ion concentrations of 0 μg/L and 20 μg/L, respectively, in a case where the excitation wavelength and the emission wavelength are 264 nm and 400 nm: a change in the fluorescence intensity (F. I) with the reaction time; and a change in the absolute value of the fluorescence intensity difference between the fluorescence intensity when the bromate ion concentration is 0 μg/L and that when the bromate ion concentration is 20 μg/L (ΔF. I.). FIG. 5B shows the same in a case where the excitation wavelength and the emission wavelength are 300 nm and 400 nm; and FIG. 5C shows the same in a case where the excitation wavelength and the emission wavelength are 300 nm and 480 nm. A time when hydrochloric acid having a concentration of 3 mol/L [N] is added is denoted as zero minute in the reaction time. For the respective peak wavelengths, the following have been measured about each of the sample the bromate ion concentration of which is 0 μg/L, and the sample the bromate ion concentration of which is 20 μg/L: a change in the fluorescence intensity with the reaction time, and a change in the fluorescence intensity difference with the reaction time. As a result, as shown in FIGS. 5A, 5B and 5C, for the respective peak wavelengths, it has been verified that the fluorescence intensity difference is stabilized after 10 minutes. Therefore, the fluorescence intensity is measured with a reaction time equivalent to that under the conventional measuring condition.

Figure 6A:
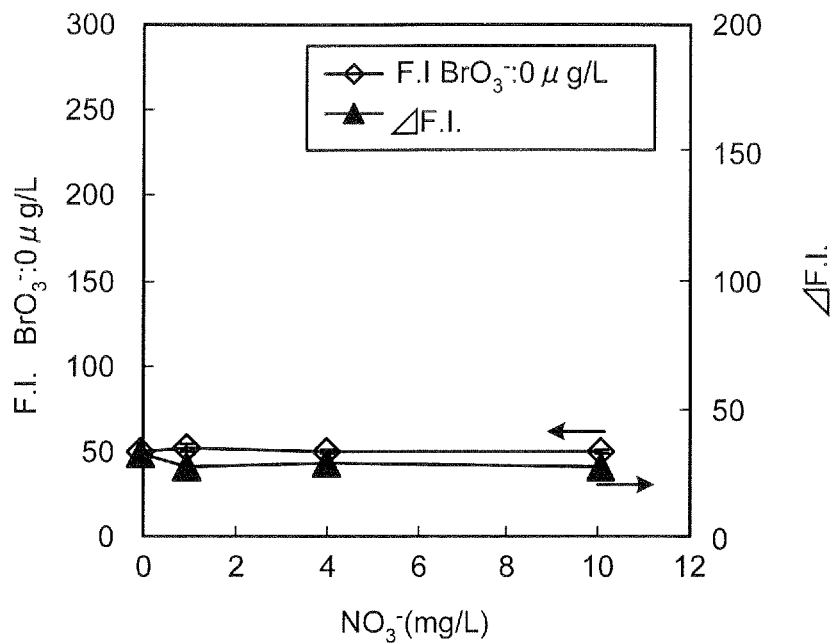
FIG. 6A is a graph showing the following in a case where the excitation wavelength and the emission wavelength are 264 nm and 400 nm: a change in the fluorescence intensity (F. I.) following a change in the concentration of nitrate ions; and a change in the absolute value of the fluorescence intensity difference between the fluorescence intensity when the bromate ion concentration is 0 μg/L, and that when the bromate ion concentration is 20 μg/L (ΔF. I.)
Figure 6B:
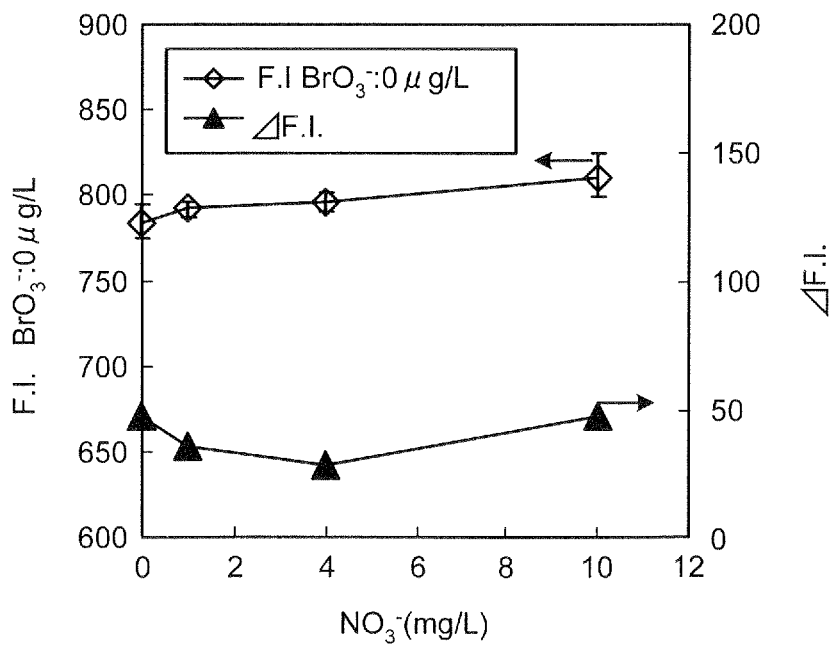
FIG. 6B is a graph showing the following in a case where the excitation wavelength and the emission wavelength are 300 nm and 480 nm: a change in the fluorescence intensity (F. I.) following a change in the concentration of nitrate ions; and a change in the absolute value of the fluorescence intensity difference between the fluorescence intensity when the bromate ion concentration is 0 μg/L, and that when the bromate ion concentration is 20 μg/L (ΔF. I.)

The inventors have evaluated an effect of nitrate ions onto the fluorescence intensity when the excitation wavelength and the emission wavelength are set to 264 nm and 400 nm, respectively. FIG. 6A is a graph showing the following in a case where the excitation wavelength and the emission wavelength are 264 nm and 400 nm, respectively: a change in the fluorescence intensity (F. I.) following a change in the concentration of nitrate ions ($NO_3^-$) when the bromate ion concentration is 0 μg/L; and a change in the absolute value of the fluorescence intensity difference between the fluorescence intensity when the bromate ion concentration is 0 μg/L, and that when the bromate ion concentration is 20 μg/L (ΔF. I.). FIG. 6B shows the same in a case where the excitation wavelength and the emission wavelength are 300 nm and 480 nm, respectively. As shown in FIG. 6B, when the excitation wavelength and the emission wavelength are 300 nm and 480 nm, respectively, which are the conventional measuring wavelengths, a variability in the fluorescence intensity following the change in the nitrate ion concentration is large, and further the slope value of the intensity change also fluctuates. Thus, it is difficult to calculate the bromate ion concentration precisely. On the other hand, as shown in FIG. 6A, when the excitation wavelength and the emission wavelength are 264 nm and 400 nm, respectively, which are one of the newly-identified peak wavelengths, a variability in the fluorescence intensity following the change in the nitrate ion concentration is small, and the slope value does not fluctuate. Thus, the bromate ion concentration can be precisely calculated. From this matter, it has been found out that when the excitation wavelength and the emission wavelength are set to 264 nm and 400 nm, respectively, the bromate ion concentration can be precisely measured without being affected by nitrate ions. It has also been verified, though not shown in figures, that the bromate ion concentration can be precisely measured without being affected by nitrate ions when the excitation wavelength and the emission wavelength are 300 nm and 400 nm, respectively.

Figure 7:
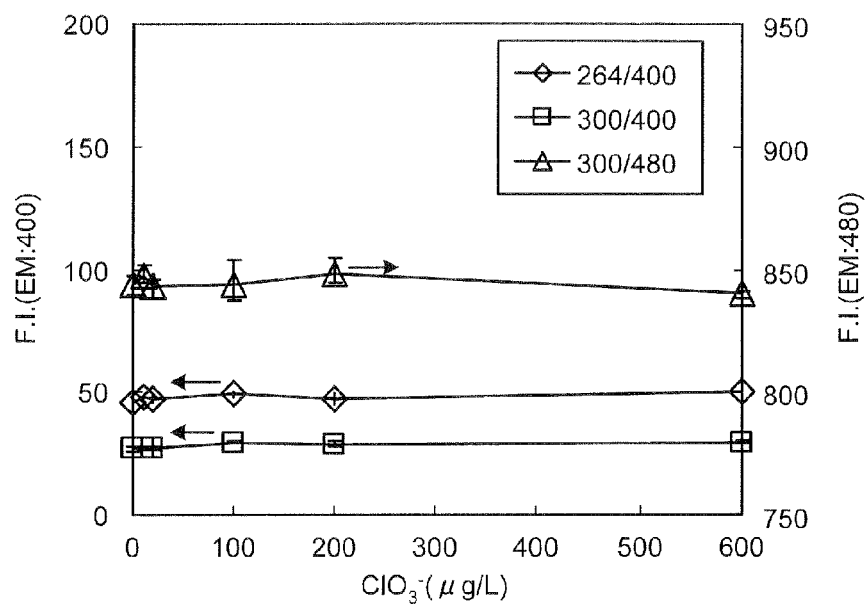
FIG. 7 is a graph showing a change in the fluorescence intensity (F. I.) when the concentration of bromate ions is 0 μg/L relative to a change in the concentration of chlorate ions for respective peak wavelengths.

When a raw water contains free chlorine, chlorate ions ($ClO_3^-$) are generated therein by ozone treatment. Thus, the inventors have measured, about a solution having a bromate ion concentration of 0 μg/L, a change in the fluorescence intensity relative to a change in the concentration of chlorate ions for the respective peak wavelengths. FIG. 7 is a graph showing the change in the fluorescence intensity (F. I.) when the bromate ion concentration is 0 μg/L relative to the change in the chlorate ion concentration for the respective peak wavelengths. As shown in FIG. 7, the fluorescence intensity for the respective peak wavelengths is not largely changed even when the chlorate ion concentration is changed. From this matter, it has been verified that chlorate ions are not a substance that interferes a precise measurement of the fluorescence intensity.

Figure 8:
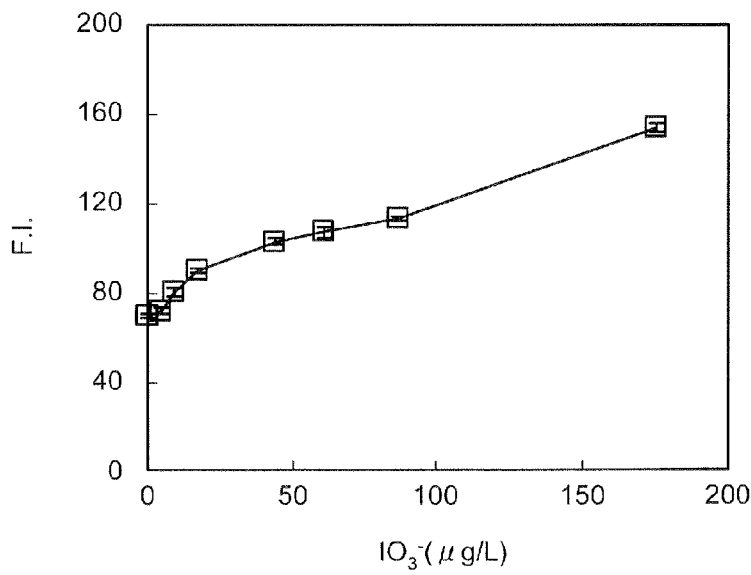
FIG. 8 is a graph showing a change in the fluorescence intensity (F. I.) when the concentration of bromate ions is 0 μg/L relative to a change in the concentration of iodate ions.

When a raw water is treated by the ozonated process, iodine-containing byproducts, such as iodate ions, may be generated. Specifically, a water treated by the ozonated process may contain iodate ions at a concentration of about 0 to 30 μg/L ("Investigation report on toxicity, behavior, and its reduction of chemical substances in tap water", Health and Labour Sciences Research Grant (Life Safety General Research Projects) in 1999, pp. 2160-2168). Thus, the inventors of the present invention have measured, about a solution having a bromate ion concentration of 0 μg/L, a change in the fluorescence intensity relative to a change in the concentration of iodate ions. FIG. 8 is a graph showing the change in the fluorescence intensity (F. I.) when the concentration of bromate ions is 0 μg/L relative to the change in the iodate ion concentration. As shown in FIG. 8, the fluorescence intensity increases irregularly as the iodate ion concentration is increased. From this matter, it has been verified that iodate ions interfere a precise measurement of the fluorescence intensity.

Figure 9:
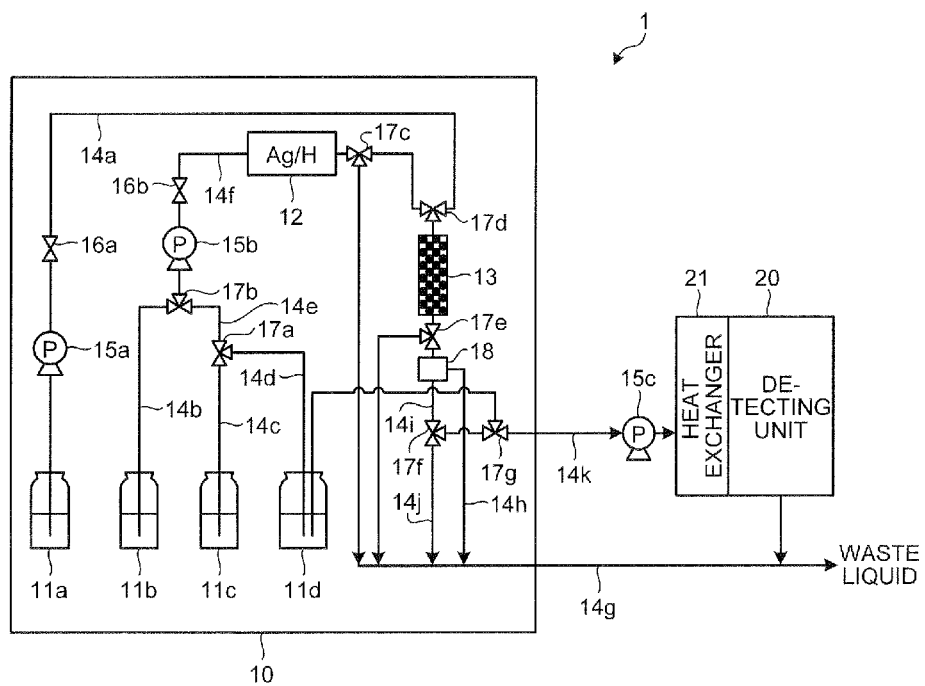
FIG. 9 is a schematic view illustrating the structure of a bromate ion measuring apparatus.

Thus, when the concentration of bromate ions is measured, it is desired to use, for example, a measuring apparatus as illustrated in FIG. 9 to separate and concentrate the bromate ions. FIG. 9 is a schematic view illustrating the structure of a bromate ion measuring apparatus. As illustrated in FIG. 9, the bromate ion measuring apparatus 1 mainly has a pretreatment unit 10 and a detecting unit 20. The pretreatment unit 10 has a bottle 11a for storing, as an eluate, a mixed solution of a TFP solution and hydrochloric acid; a bottle 11b for storing a test water sample containing bromate ions; a bottle 11c for storing a standard sample water prepared to have an arbitrary bromate ion concentration; a bottle 11d for storing ultrapure water; a Ag/H column 12; and an anion exchange column 13 functioning as an anion exchanger according to the invention.

The bottle 11a and the anion exchange column 13 are connected through a pipe 14a to each other. To the pipe 14a are fitted a pump 15a for sending the eluate in the bottle 11a into the anion exchange column 13 under pressure, and a solenoid valve 16a for controlling the supply of the eluate to the anion exchange column 13, and the stop thereof.

The bottles 11b, 11c and 11d are connected through pipes 14b to 14f to the anion exchange column 13. The pipes 14c and 14d are connected through a three-way valve 17a to the pipe 14e. The pipes 14b and 14e are connected through a three-way valve 17b to the pipe 14f. The three-way valve 17a switches a liquid to be supplied into the pipe 14e between the standard sample water in the bottle 11c and the ultrapure water in the bottle 11d. The three-way valve 17b switches a liquid to be supplied into the pipe 14f between the test water sample in the bottle 11b and the standard sample water or ultrapure water supplied from the pipe 14e.

The following are fitted to the pipe 14f: a pump 15b for sending any one of the test water sample, the standard sample water, and the ultrapure water into the anion exchange column 13 under pressure; a solenoid valve 16b for controlling the supply of any one of the test water sample, the standard sample water, and the ultrapure water into the anion exchange column 13, and the stop thereof; and the Ag/H column 12.

The Ag/H column 12 is a column wherein a silver type cation exchange column is combined with a hydrogen type cation exchange column, and has a function of absorbing halogen contained in a liquid passed through this column. At the liquid outflow side of the Ag/H column 12, a three-way valve 17c is arranged. The three-way valve 17c switches a channel for a liquid discharged from the Ag/H column 12 between a direction into the anion exchange column 13 and a direction into/along a pipe 14g, for waste liquid, that discharges a liquid outside.

The anion exchange column 13 has a function of absorbing bromate ions selectively without absorbing iodate ions. In the present embodiment, the anion exchange column 13 is made of a strong anion exchange column having, as a sorbent, a polymer subjected to a processing for decreasing hydrophobicity and having, as functional groups, a quaternary amine. At the liquid inflow side of the anion exchange column 13, a three-way valve 17d is arranged. The three-way valve 17d switches a liquid to be supplied into the anion exchange column 13 between a liquid from the pipe 14a and a liquid from the pipe 14f. At the liquid outflow side of the anion exchange column 13, a three-way valve 17e is arranged. The three-way valve 17e switches a channel for a liquid discharged from the anion exchange column 13 between a direction into a bottle 18 and a direction into/along the pipe 14g for waste liquid.

The bottle 18 is a bottle for temporarily storing a liquid discharged from the anion exchange column 13. To the bottle 18 are fitted a pipe 14i, and a pipe 14h for discharging an overflow liquid to the pipe 14g. A three-way valve 17f is connected to the pipe 14i. The three-way valve 17f switches a channel for the liquid in the bottle 18 that is discharged from the pipe 14i between a direction into/along the pipe 14j for discharging a liquid into the pipe 14g for water liquid, and a direction into/along a detecting pipe 14k.

To the detecting pipe 14k are fitted a three-way valve 17g and a pump 15c. The three-way valve 17g switches a liquid to be supplied into the pump 15c between the ultrapure water in the bottle 11d and the liquid in the bottle 18. The pump 15c sends a liquid supplied through the three-way valve 17g, under pressure, into the detecting unit 20.

The detecting unit 20 is a device for measuring the fluorescence intensity of a solution by use of the flow injection method. Specifically, the detecting unit 20 measures the fluorescence intensity of a solution sent under pressure by the pump 15c. The solution about which the measurement is ended is discharged into the pipe 14g for waste liquid. By the measurement of the fluorescence intensity with the flow injection method, the fluorescence intensity of the solution can be continuously and automatically measured. In order to control the measurement precision of the fluorescence intensity into a constant level, a heat exchanger 21 is arranged in the detecting unit 20. In order to control the measurement precision of the fluorescence intensity into a constant level, it is allowable to control the three-way valve 17g, thereby introducing the ultrapure water in the bottle 11d through the detecting pipe 14k into a pipe in the detecting unit 20, and washing the pipe in the detecting unit 20 whenever a measurement is made.

The bromate ion measuring apparatus 1, which has this structure, makes a measurement of any test water sample as follows: when the bromate ion concentration in the test water sample is measured, the solenoid valve 16b is first made into an open state and then the liquid channels are controlled through the three-way valves 17a to 17e. The pump 15b is further driven, thereby introducing the ultrapure water in the bottle 11d into the Ag/H column 12 and the anion exchange column 13 and discharging the ultrapure water passed through the Ag/H column 12 and the anion exchange column 13 into the pipe 14g for waste liquid. Next, the driving of the pump 15b is stopped and the solenoid valve 16b is made into a close state. Thereafter, the solenoid valve 16a is made into an open state, the liquid channels are controlled through the three-way valves 17d to 17g, and the pump 15a is driven, thereby introducing the eluate into the anion exchange column 13 and supplying the eluate discharged from the anion exchange column 13 into the detecting unit 20. In the detecting unit 20, the fluorescence intensity of the eluate is measured, thereby making it possible to detect the fluorescence intensity when the bromate ion concentration is 0 (zero-point adjustment).

Next, the driving of the pump 15a is stopped and the solenoid valve 16a is made into a close state. Thereafter, the solenoid valve 16b is made into an open state, the liquid channels are controlled through the three-way valves 17a to 17e, and the pump 15b is driven, thereby introducing the standard sample water in the bottle 11c into the Ag/H column 12 and the anion exchange column 13, and discharging the standard sample water passed through the anion exchange column 13 into the pipe 14g for waste liquid. By this processing, the bromate ions in the standard sample water are absorbed onto the anion exchange column 13 to be separated and concentrated. Next, the driving of the pump 15b is stopped, and the solenoid valve 16b is made into a close state. Thereafter, the solenoid valve 16a is made into an open state, the liquid channels are controlled through the three-way valves 17d to 17g, and the pump 15a is driven, thereby introducing the eluate into the anion exchange column 13 and supplying the eluate discharged from the anion exchange column 13 into the detecting unit 20. By this processing, the bromate ions in the standard sample water that are absorbed on the anion exchange column 13 are eluted out into the eluate, and supplied into the detecting unit 20. In the detecting unit 20, the fluorescence intensity of the eluate is measured, thereby making it possible to detect the fluorescence intensity corresponding to the bromate ion concentration in the standard sample water.

Next, from the fluorescence intensity when the bromate ion concentration is 0, and the fluorescence intensity corresponding to the bromate ion concentration in the standard sample water, the detecting unit 20 prepares a calibration curve showing a corresponding relationship between the concentration of bromate ions and the fluorescence intensity. This calibration-curve-preparing processing, and the processing previous thereto may be conducted in advance, or may be conducted whenever any one of the respective bromate ion concentrations in test water samples is measured.

After the finish of the preparation of the calibration curve, the solenoid valve 16b is next made into an open state, the liquid channels are controlled through the three-way valves 17a to 17e, and the pump 15b is driven, thereby introducing the test water sample in the bottle 11b into the Ag/H column 12 and the anion exchange column 13, and discharging the test water sample passed through the Ag/H column 12 and the anion exchange column 13 into the pipe 14g for water liquid. By this processing, the bromate ions in the test water sample are absorbed onto the anion exchange column 13 to be separated and concentrated. Next, the driving of the pump 15b is stopped and the solenoid valve 16b is made into a close state. Thereafter, the solenoid valve 16a is made into an open state, and the pump 15a is driven, thereby introducing the eluate into the anion exchange column 13 and supplying the eluate discharged from the anion exchange column 13 into the detecting unit 20. By this processing, the bromate ions in the test water sample that are passed through the anion exchange column 13 are eluted out into the eluate, and supplied into the detecting unit 20. In the detecting unit 20, the fluorescence intensity of the eluate is measured, and on the basis of the calibration curve the bromate ion concentration corresponding to the measured fluorescence intensity is calculated. According to the above-mentioned process-flow, the bromate ion concentration in the test water sample can be measured.

In the present example, the effect of removing iodate ions by an anion exchange column was verified. Specifically, about each of tap waters A, B and C each containing iodate ions at an arbitrarily concentration, the following operation was made: free chlorine was removed therefrom, and 150 mL of the tap water was introduced into an Ag/H column; and subsequently the water was introduced into an anion exchange column to absorb a target substance onto the anion exchange column. Thereafter, the target substance absorbed on the anion exchange column was eluted out with 30 mL of an eluate (mixed solution of hydrochloric acid and TFP). The environmental temperature at the time of each of the absorption and the eluate was set to room temperature. At the time of the measurement, the sample temperature was cooled to 18.0° C. The respective concentrations of the iodate ions before and after the concentration, and the removal rate thereof are shown in Table 1 described below. As shown in Table 1, when each of all the test water samples was not introduced to the anion exchange column, that is, when bromate ions were not separated nor concentrated, a fluorescence intensity based on the iodate ions was detected in the test water sample. On the other hand, when each of all the test water samples was passed through the anion exchange column, that is, when bromate ions were separated and concentrated, no fluorescence intensity based on the iodate ions was detected in the test water sample. Moreover, no iodate ions were collected from the anion exchange column. It was verified from this matter that when a test water sample is introduced into an anion exchange column, bromate ions can be separated from iodate ions, and further concentrated. Therefore, by introducing a test water sample into an anion exchange column, bromate ions can be measured with a higher precision.

TABLE 1

| | Iodate ions | | |
|---|---|---|---|
| Test water sample name | Before concentration (μg/L) | After concentration (μg/L) | Collection rate (%) |
| Tap water A | 21 | 0 | 0 |
| Tap water B | 16 | 0 | 0 |
| Tap water C | 31 | 0 | 0 |

As is evident from the above description, the bromate ion measuring method of the embodiment of the invention includes a first step of introducing a test water sample to an anion exchanger that selectively absorbs bromate ions; a second step of introducing, to the anion exchanger, a hydrochloric acid solution containing a fluorescent substance, a fluorescence intensity of which is changed by the coexistence of bromate ions; a third step of measuring the fluorescence intensity of the fluorescent substance contained in the hydrochloric acid solution discharged from the anion exchanger; and a fourth step of using a calibration curve, which shows a relationship between the fluorescence intensity of the fluorescent substance and the concentration of the bromate ions, to calculate the concentration of the bromate ions that corresponds to the measured fluorescence intensity; wherein the third step includes the step of measuring the fluorescence intensity at any one of a case where the excitation wavelength and the emission wavelength are 264 nm and 400 nm, respectively, a case where the excitation wavelength and the emission wavelength are 264 nm and 480 nm, respectively, and a case where the excitation wavelength and the emission wavelength are 300 nm and 400 nm, respectively; therefore, the bromate ion concentration can be measured with a high precision while the concentration of hydrochloric acid necessary for the measurement is lowered.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for measuring bromate ions, comprising:
a first step of introducing a test water sample to an anion exchanger that selectively absorbs bromate ions;
a second step of introducing, to the anion exchanger, a hydrochloric acid solution containing a fluorescent substance, a fluorescence intensity of which is changed by the coexistence of bromate ions;
a third step of measuring the fluorescence intensity of the fluorescent substance contained in the hydrochloric acid solution discharged from the anion exchanger; and
a fourth step of using a calibration curve, which shows a relationship between the fluorescence intensity of the fluorescent substance and the concentration of the bromate ions, to calculate a concentration of the bromate ions that corresponds to the measured fluorescence intensity,
wherein the third step comprises measuring the fluorescence intensity in one of (a) a case where the excitation wavelength is 264 nm and the emission wavelength is 400 nm, (b) a case where the excitation wavelength is 264 nm and the emission wavelength is 480 nm, and (c) a case where the excitation wavelength is 300 nm and the emission wavelength is 400 nm.

2. The method for measuring bromate ions according to claim 1, wherein the third step comprises the step of using a flow injection method to measure the fluorescence intensity of the fluorescent substance.

3. The method for measuring bromate ions according to claim 1, wherein the anion exchanger is a strong anion exchanger having, as a functional group thereof, a quaternary amine.

4. The method for measuring bromate ions according to claim 2, wherein the anion exchanger is a strong anion exchanger having, as a functional group thereof, a quaternary amine.

5. An apparatus for measuring bromate ions, comprising:
a unit that introduces a test water sample to an exchanger that selectively absorbs bromate ions;
a unit that introduces, to the anion exchanger, a hydrochloric acid solution containing a fluorescent substance, a fluorescence intensity of which is changed by the coexistence of bromate ions;
a unit that measures the fluorescence intensity of the fluorescent substance contained in the hydrochloric acid solution discharged from the anion exchanger; and
a unit that uses a calibration curve, which shows a relationship between the fluorescence intensity of the fluorescent substance and the concentration of the bromate ions, to calculate the concentration of the bromate ions that corresponds to the measured fluorescence intensity,
wherein the fluorescence intensity measuring unit makes a measurement of the fluorescence intensity in one of (a) a case where the excitation wavelength and the emission wavelength are 264 nm and 400 nm, respectively, (b) a case where the excitation wavelength and the emission wavelength are 264 nm and 480 nm, respectively, and (c) a case where the excitation wavelength and the emission wavelength are 300 nm and 400 nm, respectively.

* * * * *

UNITED STATES PATENT AND TRADEMARK OFFICE
CERTIFICATE OF CORRECTION

PATENT NO. : 8,748,189 B2  
APPLICATION NO. : 13/597664  
DATED : June 10, 2014  
INVENTOR(S) : Natsumi Kita and Eri Hasegawa Page 1 of 1

It is certified that error appears in the above-identified patent and that said Letters Patent is hereby corrected as shown below:

Title Page, Item (30) Foreign Application Priority Data

Please insert the following: --June 18, 2012 (JP) 2012-136846--

Signed and Sealed this  
Twenty-third Day of December, 2014

Michelle K. Lee  
*Deputy Director of the United States Patent and Trademark Office*